(12) United States Patent
Maiya et al.

(10) Patent No.: US 10,796,130 B2
(45) Date of Patent: Oct. 6, 2020

(54) IMAGE PROCESSING APPARATUS

(71) Applicant: NIKON CORPORATION, Tokyo (JP)

(72) Inventors: Nobuhiko Maiya, Yokohama (JP); Masafumi Yamashita, Fujisawa (JP); Shoko Yamasaki, Tokyo (JP); Yosuke Otsubo, Tokyo (JP); Shunsuke Takei, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 66 days.

(21) Appl. No.: 16/060,247

(22) PCT Filed: Dec. 22, 2015

(86) PCT No.: PCT/JP2015/085853
§ 371 (c)(1),
(2) Date: Jun. 7, 2018

(87) PCT Pub. No.: WO2017/109860
PCT Pub. Date: Jun. 29, 2017

(65) Prior Publication Data
US 2018/0349675 A1 Dec. 6, 2018

(51) Int. Cl.
*G06K 9/00* (2006.01)
*C12M 1/34* (2006.01)
(Continued)

(52) U.S. Cl.
CPC ........ *G06K 9/00147* (2013.01); *C12M 1/34* (2013.01); *G02B 21/00* (2013.01); *G06K 9/0014* (2013.01);
(Continued)

(58) Field of Classification Search
None
See application file for complete search history.

(56) References Cited

U.S. PATENT DOCUMENTS 6,198,839 B1 * 3/2001 Kuan ............... G01N 15/1475
128/922
7,369,696 B2 * 5/2008 Arini ............... G01N 15/1475
382/128
(Continued)

FOREIGN PATENT DOCUMENTS

EP 1865315 A1 12/2007
EP 2 992 824 A1 3/2016
(Continued)

OTHER PUBLICATIONS

Apr. 23, 2019 Office Action issued in Japanese Patent Application No. 2017-557557.
(Continued)

*Primary Examiner* — Shervin K Nakhjavan
(74) *Attorney, Agent, or Firm* — Oliff PLC

(57) ABSTRACT

An image processing apparatus includes a cell image acquisition unit configured to acquire a cell image captured with cells, a characteristic amount calculation unit configured to calculate a plurality of types of characteristic amounts on the cell image acquired by the cell image acquisition unit, and a correlation extraction unit configured to extract specific correlations from among a plurality of correlations among the characteristic amounts calculated by the characteristic amount calculation unit, based on likelihood of the characteristic amounts.

10 Claims, 13 Drawing Sheets

(51) Int. Cl.
*G06T 1/00* (2006.01)
*G02B 21/00* (2006.01)
*G06T 7/00* (2017.01)

(52) U.S. Cl.
CPC .............. *G06T 1/00* (2013.01); *G06T 7/0012* (2013.01); *G06T 2207/10056* (2013.01); *G06T 2207/20076* (2013.01); *G06T 2207/30024* (2013.01)

(56) References Cited

U.S. PATENT DOCUMENTS

| | | | |
|---|---|---|---|
| 9,280,698 B2 | 3/2016 | Kll et al. | |
| 9,488,639 B2* | 11/2016 | Lange | G06K 9/00147 |
| 9,536,043 B2* | 1/2017 | Amir | G06K 9/00 |
| 9,779,283 B2* | 10/2017 | Bhargava | G06K 9/6228 |
| 10,055,844 B2* | 8/2018 | Hamada | G06T 7/0012 |
| 10,197,782 B2* | 2/2019 | Kataoka | G06T 7/0016 |
| 2008/0016015 A1* | 1/2008 | Perner | G06K 9/00127 706/20 |
| 2008/0176276 A1* | 7/2008 | Arai | G01N 33/5005 435/40.5 |
| 2008/0279441 A1 | 11/2008 | Matsuo et al. | |
| 2009/0190821 A1* | 7/2009 | Marugame | G06K 9/00127 382/133 |
| 2009/0324050 A1* | 12/2009 | Takagi | G01N 15/1463 382/133 |
| 2010/0184093 A1* | 7/2010 | Donovan | G16H 50/50 435/7.21 |
| 2011/0014647 A1* | 1/2011 | Dorian | G01N 33/5091 435/40.5 |
| 2011/0136152 A1* | 6/2011 | Lin | G01N 15/1475 435/7.25 |
| 2012/0271553 A1* | 10/2012 | McCulloch | G06K 9/00147 702/19 |
| 2014/0227682 A1* | 8/2014 | Seth | C12Q 1/70 435/5 |
| 2014/0273075 A1* | 9/2014 | Kolanko | G01N 15/1475 435/39 |
| 2015/0003716 A1* | 1/2015 | Lloyd | G06F 19/321 382/133 |
| 2015/0131889 A1* | 5/2015 | Aragaki | G06T 7/42 382/133 |
| 2015/0272461 A1 | 10/2015 | Morimoto et al. | |
| 2016/0070949 A1* | 3/2016 | Tunstall | G06K 9/0014 382/133 |
| 2016/0160169 A1* | 6/2016 | Paczkowski | G06T 7/13 506/10 |
| 2017/0350805 A1* | 12/2017 | Murata | C12M 1/34 |

FOREIGN PATENT DOCUMENTS

| | | |
|---|---|---|
| JP | 2014-085949 A | 5/2014 |
| WO | 2006/104201 A1 | 10/2006 |
| WO | 2014/178323 A1 | 11/2014 |

OTHER PUBLICATIONS

Jerome Friedman et al.; Biostatistics (2008), 9, 3, pp. 432-441, "Sparse inverse covariance estimation with the graphical lasso"; Published Dec. 12, 2007.

Tsuyoshi Idé et al.; "Computing Correlation Anomaly Scores using Stochastic Nearest Neighbors"; Proceedings of the Seventh IEEE International Conference on Data Mining; Oct. 28-31, 2007, pp. 523-528.

José Angel Pineda-Pardo et. al; "Guiding functional connectivity estimation by structural connectivity in MEG: an application to discrimination of conditions of mild cognitive impairment"; NeuroImage 101 (2014); pp. 765-777.

Mar. 22, 2016 International Search Report issued in International Patent Application No. PCT/JP2015/085853.

Mar. 22, 2016 Written Opinion issued in International Patent Application No. PCT/JP2015/085853.

Jul. 24, 2019 Search Report issued in European Patent Application No. 15911298.6.

Puniyani et al.; "Inferring Gene Interaction Networks from ISH Images via Kernelized Graphical Models;" Computer Vision ECCV 2012; Springer-Verlag Berlin Heidelberg; 2012; pp. 72-85; XP047019136.

Wang; "Integrative Analysis of Mult-Modality Data in Cancer;" Dissertation; The Ohio State University; Jan. 1, 2015; XP055355084; URL:https://etd.ohiolink.edu/!etd.send_file?accession=osu1429791373&disposition=inline.

Feb. 4, 2020 Office Action issued in Japanese Patent Application No. 2017-557557.

* cited by examiner

| TYPE | FUNCTION |
|---|---|
| PROTEIN A | TRANSCRIPTION FACTOR (ACTIVATION) |
| PROTEIN B | KINASE |
| ⋮ | ⋮ |

FIG. 12

| NW ELEMENT | CHARACTERISTIC AMOUNT | CHANGE IN CHARACTERISTIC AMOUNT | BIOLOGICAL IMPLICATION |
|---|---|---|---|
| TRANSCRIPTION FACTOR (ACTIVATION) | TOTAL INTRANUCLEAR LUMINANCE VALUE /TOTAL INTRACELL LUMINANCE VALUE | Up | TRANSACTIVATION |
| TRANSCRIPTION FACTOR (REPRESSION) | TOTAL INTRANUCLEAR LUMINANCE VALUE /TOTAL INTRACELL LUMINANCE VALUE | Up | TRANSREPRESSION |
| KINASE | TOTAL INTRACYTOPLASMIC LUMINANCE VALUE /TOTAL INTRACELL LUMINANCE VALUE | Up | ACTIVATION OF PHOSPHORYLATION |
| PHOSPHATASE | TOTAL INTRACYTOPLASMIC LUMINANCE VALUE /TOTAL INTRACELL LUMINANCE VALUE | Up | ACTIVATION OF DEPHOSPHORYLATION |
| MITOCHONDRION | FRAGMENTATION RATE | Up | ACTIVATION OF DIVISION |
| | | Up | INCREASE IN OXDATIVE STRESS |
| | | Up | INCREASE IN MITOPHAGY |

FIG. 13

MICRO

1. DETECTION OF CHANGE IN EDGE PARTICLE SIZE: CHANGE IN RELATIONSHIP $$Score_{ij} = |\hat{P}_{ij}^1 - \hat{P}_{ij}^2|$$

2. DETECTION OF CHANGE IN NODE PARTICLE SIZE: CHANGE IN VARIABLE

3. DETECTION OF CHANGE IN CLUSTER PARTICLE SIZE: CHANGE IN Ego

4. DETECTION OF CHANGE IN NETWORK PARTICLE SIZE: CHANGE IN NETWORK

MACRO

FIG. 14

|  |  | KNOWLEDGE BASE NETWORK | |
|---|---|---|---|
|  |  | 1 | 0 |
| PREDICTION NETWORK | 1 | TP | FP |
|  | 0 | FN | TN |

BOUND = 1
NOT BOUND = 0

FIG. 16

IMAGE PROCESSING APPARATUS

TECHNICAL FIELD

The present invention relates to an image processing apparatus.

BACKGROUND ART

In biological science, medical science, and the like, it is known that there is a correlation, for example, between a state of health, disease, or the like of a living organism and a state of cells, organelles inside the cells, and the like. Thus, analyzing the correlation between these is one technique for solving various issues in biological science, medical science, and the like. Further, for example, analyzing transduction pathways of information transmitted between cells or within cells can be helpful for research relating to biosensors in industrial applications, in the manufacture of drugs with the aim of preventing disease, and the like. In various analysis techniques relating to cells and tissue slices, techniques are known that use image processing, for example (see Patent Document 1, for example).

CITATION LIST

Patent Literature

Patent Document 1: U.S. Pat. No. 0,228,069

SUMMARY OF INVENTION

Technical Problem

However, when image processing is performed on an image captured with cells, and the acquired information is used to calculate interactions within the cells or interactions among the cells, the acquired information becomes greater in amount. A large amount of computation is thus required for acquiring correlations. Such a large amount of computation might result in an analysis failure.

In view of the above described problems, the present invention has an object to provide an image processing apparatus capable of reducing analysis failures.

Solution to Problem

To solve the above described problems, an image processing apparatus according to one aspect of the present invention includes a cell image acquisition unit configured to acquire a cell image captured with cells, a characteristic amount calculation unit configured to calculate a plurality of types of characteristic amounts on the cell image acquired by the cell image acquisition unit, and a correlation extraction unit configured to extract specific correlations from among a plurality of correlations among the characteristic amounts calculated by the characteristic amount calculation unit, based on likelihood of the characteristic amounts.

Advantageous Effects of Invention

With the present invention, analysis failures due to image processing can be reduced.

BRIEF DESCRIPTION OF DRAWINGS

FIG. 12 is a table illustrating an example of a protein annotation database according to the present embodiment.

FIG. 13 is a table illustrating an example of a characteristic amount annotation database according to the present embodiment.

FIG. 14 is a drawing illustrating an example of a model for comparing characteristic amount networks, according to the present embodiment.

FIG. 16 is a drawing illustrating a relationship between a knowledge base network and a prediction network, with respect to whether binding is present in a characteristic amount network, according to the present embodiment.

DESCRIPTION OF EMBODIMENTS

Embodiments

Figure 1:
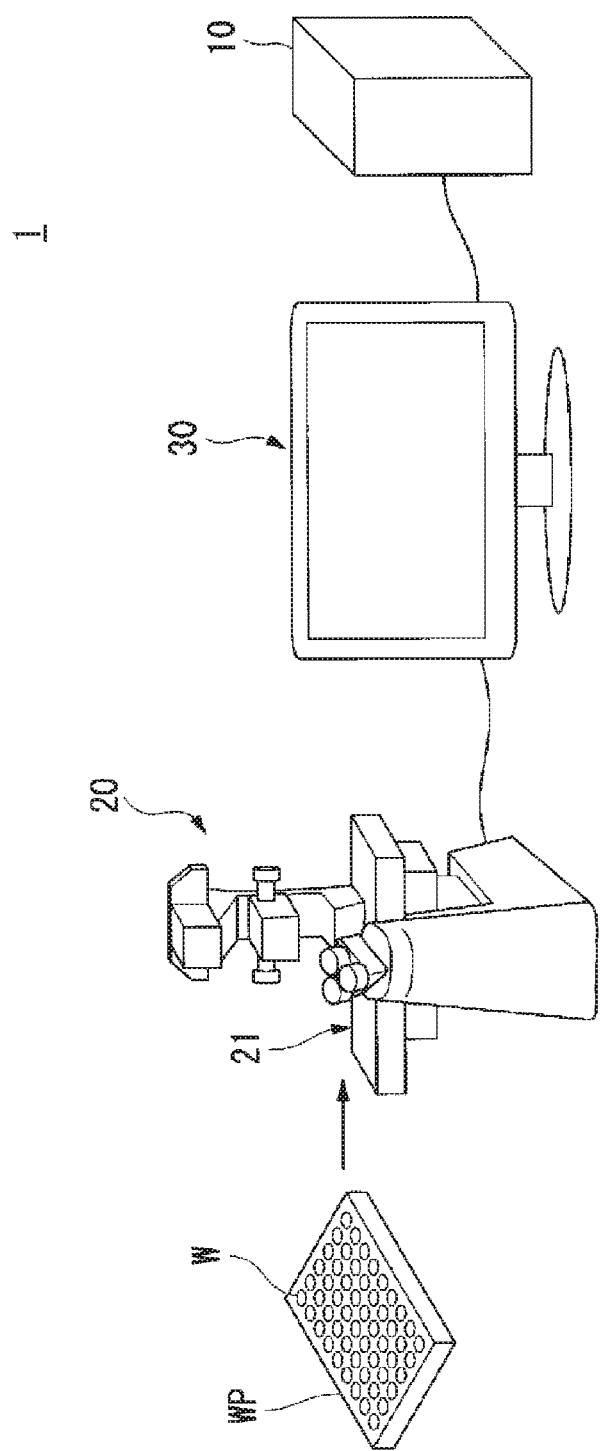
FIG. 1 is a schematic view illustrating an example of a configuration of a microscope observation system according to an embodiment of the present invention.

Embodiments of the present invention will now be described herein with reference to the drawings. FIG. 1 is a schematic view illustrating an example of a configuration of a microscope observation system 1 according to an embodiment of the present invention.

The microscope observation system 1 is configured to perform image processing on an image captured with cells, for example. An image captured with cells, for example, will also be hereinafter simply referred to as a cell image. The microscope observation system 1 includes an image processing apparatus 10, a microscope apparatus 20, and a display unit 30.

The microscope apparatus 20 is a biological microscope, and includes an electromotive stage 21 and an imaging unit 22. With the electromotive stage 21, a position of an object to be captured can be moved as desired in a predetermined direction (e.g., direction on a two-dimensional plane extending in a horizontal direction). The imaging unit 22 includes an imaging element, such as a charge-coupled device (CCD) or a complementary MOS (CMOS), and is configured to capture the object on the electromotive stage 21. The microscope apparatus 20 may not include the electromotive stage 21, but may include a stage that does not move in the predetermined direction.

More specifically, the microscope apparatus 20 has functions of other microscopes, such as a differential interference contrast microscope (DIC), a phase contrast microscope, a fluorescence microscope, a confocal microscope, and a super-resolution microscope, for example. The microscope apparatus 20 captures images of a culture vessel placed on the electromotive stage 21. The culture vessel is a well plate WP, for example. The microscope apparatus 20 irradiates cells cultured inside a plurality of wells W provided in the well plate WP with light, and thus captures an image of the transmitted light transmitted through the cells, as the image of the cells. In this way, an image of the cells can be obtained, such as a transmission DIC image, a phase contrast image, a dark field image, and a bright field image. In addition, by irradiating the cells with excitation light that excites a fluorescent material, an image of fluorescence emitted from the fluorescent material can be captured, as the image of the cells. Alternatively, the microscope apparatus 20 may capture, as the above-described image of the cells, an image of fluorescence emitted from the fluorescent material itself incorporated in a biological material, or of fluorescence emitted by a material having chromophores being combined with the biological material. In this way, the microscope observation system 1 can acquire a fluorescent picture image, a confocal image, and a super-resolution image. The method for acquiring an image of cells is not limited to the method using an optical microscope. For example, an electron microscope may be used. An image of cells described later may be acquired through a different method to acquire correlations. That is, a type of an image of cells may be appropriately selected. The cells referred in the present embodiment include, for example, primary cultured cells, subculture cells, tissue sections, and the like. To observe cells, samples to be observed may be an aggregation of cells, a tissue sample, an organ, or a solid (e.g., animal) for acquiring an image of the cells. Note that the state of the cells is not particularly limited to a specific state, and may be a living state or may be a fixed state. Specifically, the state may be either "in-vivo" or "in-vitro". Obviously, information on the living state and information on the fixed state may be combined.

A cell state may be appropriately selected by purpose. For example, a fixed state or a non-fixed state may be selected depending on a type (e.g., protein or organelle) to be discerned in a structure in a cell. To acquire dynamic behavior of a fixed cell, a plurality of fixed cells are created under different conditions. The dynamic behavior is thus acquired. In a structure in a cell, a type to be discerned is not limited to a type of a nucleus.

Cells that have been subjected to processing in advance may be observed. Obviously, cells that have not yet been subjected to processing may also be observed. Cells having been subjected to immunostaining may be observed. For example, a stain may be selected in accordance with a type to be discerned in a structure in a nucleus of a cell. For a staining method, any staining method can be used. For example, various special staining mainly used for tissue staining, as well as hybridization using binding of base arrangements, can be used.

Cells may be subjected to processing with a photoprotein (e.g., photoprotein expressed from an introduced gene (e.g., luciferase gene)) for observation. For example, a photoprotein to be used may be selected in accordance with a type to be discerned in a structure in a nucleus of a cell.

Preparation for analyzing and acquiring correlations, such as means of observing cells and/or a method for staining cells, may be appropriately selected by purpose. For example, an optimum method for acquiring dynamic behavior of cells may be used to acquire dynamic information on the cells, and an optimum method for acquiring signal transmissions in cells may be used to acquire information on signal transmissions in cells. Preparation methods to be selected by purpose may differ from each other. Types of preparation to be selected by purpose may be reduced. For example, when a method for acquiring dynamic behavior of cells and a method for acquiring signal transmissions in cells differ from respective optimum methods, acquiring respective pieces of information with the different methods becomes complicated. Therefore, as long as the respective pieces of information can be fully acquired, common methods may be respectively performed for both cases, even when the common methods differ from the optimum methods.

The well plate WP includes a plurality of the wells W. In the example, the well plate WP includes 12 wells W×8 wells W, i.e., 96 wells W in total. Cells are cultured in each of the wells W under specific experimental conditions. The specific experimental conditions include a temperature, humidity, a period of culture, an elapsed time period from when a stimulus is applied, a type and strength of the applied stimulus, a presence or absence of the stimulus, induction of biological characteristics, and the like. The stimulus is, for example, a physical stimulus such as electricity, sound waves, magnetism, or light, or a chemical stimulus obtained by administering a substance, a drug, or the like. Further, the biological characteristics are characteristics indicating a stage of differentiation of the cells, a morphology, the number of the cells, and the like.

Figure 2:
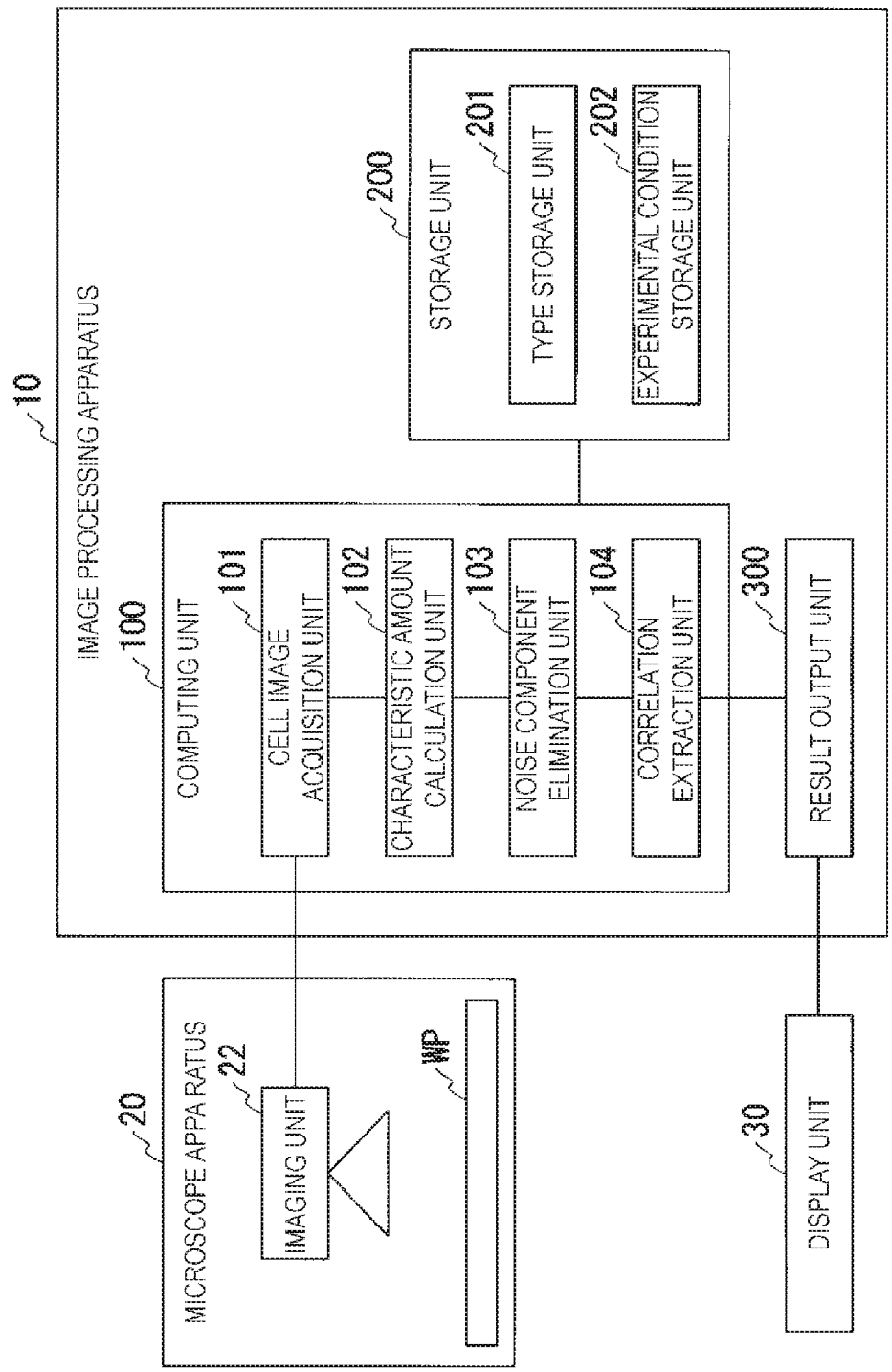
FIG. 2 is a block diagram illustrating an example of a functional configuration of units included in the image processing apparatus according to the present embodiment.

FIG. 2 is a block diagram illustrating an example of a functional configuration of units included in the image processing apparatus 10 according to the present embodiment. The image processing apparatus 10 is a computer device configured to analyze an image acquired by the microscope apparatus 20. The image processing apparatus 10 includes a computing unit 100, a storage unit 200, and a result output unit 300. Note that the images to be subjected to image processing by the image processing apparatus 10 are not limited to the images captured by the microscope apparatus 20, and may be, for example, images stored in advance in the storage unit 200 included in the image processing apparatus 10, or may be images stored in advance in an external storage device (not illustrated).

The computing unit 100 functions when a program stored in the storage unit 200 is executed by a processor. Further, some or all of each of the functional portions of the computing unit 110 may include hardware, such as Large Scale Integration (LSI) or an Application Specific Integrated Circuit (ASIC). The computing unit 100 includes a cell image acquisition unit 101, a characteristic amount calculation unit 102, a noise component elimination unit 103, and a correlation extraction unit 104.

The cell image acquisition unit 101 is configured to acquire a cell image captured by the imaging unit 22, and to supply the acquired cell image to 102. Cell images to be acquired by the cell image acquisition unit 101 include a plurality of images captured with cells in various culturing states in a time series manner, and a plurality of images of cells cultured under various experimental conditions.

The characteristic amount calculation unit 102 is configured to calculate a plurality of types of characteristic amounts on a cell image supplied by the cell image acquisition unit 101. The characteristic amounts include luminance, area, and variance, for example, on the cell image.

That is, the characteristic amounts are characteristics derived from information acquired from the captured cell image. For example, a luminance distribution in an acquired image is calculated. Such a plurality of images that are captured in a time series manner or that differ due to changes in a cell state, such as differentiation, may be used. Based on a change in calculated luminance distribution within a predetermined period or a change in calculated luminance distribution along with a change in cell state, such as differentiation, position information indicative of a change in luminance that differs from other luminance may be acquired. Such a change in luminance may be used as a characteristic amount. In this case, in addition to a change in time, a plurality of different images indicating how a cell state, such as differentiation, has changed may be used. Position information indicative of how various luminance has changed may be used as a characteristic amount. For example, behavior of cells within a predetermined period or behavior of cells along with a change in cell state, such as differentiation, may be used. Additionally, a change in cell shape within a predetermined period or a change in cell shape along with a change in cell state, such as differentiation, may be used. When neither a change within a predetermined period nor a change along with a change in cell state, such as differentiation, can be observed in a captured cell image, a fact that there is no change may be used as a characteristic amount.

The noise component elimination unit 103 is configured to eliminate noise components (noise) from characteristic amounts calculated by the characteristic amount calculation unit 102.

The correlation extraction unit 104 is configured to extract, with respect to the characteristic amounts from which the noise components have been eliminated by the noise component elimination unit 103, specific correlations from among a plurality of correlations among characteristic amounts calculated by the characteristic amount calculation unit 102, based on likelihood of the characteristic amounts. The term "likelihood" used herein denotes, when a result is calculated under a predetermined condition, a numerical value representing likelihood on estimation of the predetermined condition in accordance with the result. The term "likelihood" used herein also denotes, when data follows a probability model, a cost function representing likelihood of a parameter that should be estimated.

The result output unit 300 is configured to output a result of computation performed by the computing unit 100 to the display unit 30. The result output unit 300 may output a result of computation performed by the computing unit 100 to an output device or a storage device, other than the display unit 30.

The display unit 30 is configured to display the computation result output by the result output unit 300.

A specific computation procedure performed by the computing unit 100 described above will be described with reference to FIG. 3.

Figure 3:
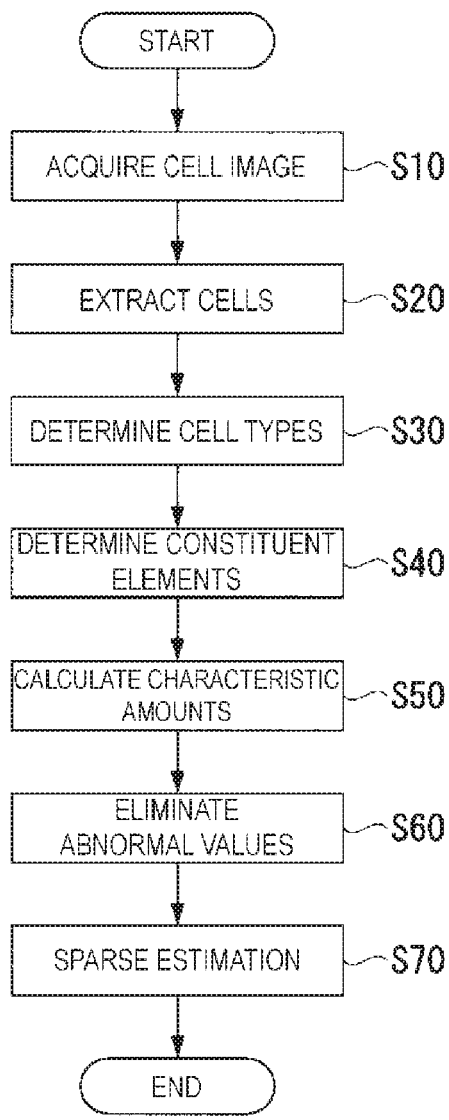
FIG. 3 is a flowchart illustrating an example of a computation procedure performed by a computing unit according to the present embodiment.

FIG. 3 is a flowchart illustrating an example of a computation procedure performed by the computing unit 100 according to the present embodiment. The computation procedure illustrated in here is merely an example. A part or whole of the computation procedure may be omitted. Another computation procedure may be added.

The cell image acquisition unit 101 acquires a cell image (Step S10). The cell image includes images of a plurality of types of biological tissues that differ in size, such as genes, proteins, and organelles. The cell image further includes information on shapes of cells. Dynamic behavior is acquired from cell images captured in various time series or from cell images under different cell states, such as differentiation. Therefore, performing an analysis using a plurality of scales on cell images ranging in cell size from intracell minute structure to cell shape, or using a plurality of scales on cell images captured in a predetermined period, on cell images that differ in time series from cell images under a cell state, such as differentiation, or on cell images that differ in dimension from cell images under different cell states, such as differentiation, can be referred to as multi-scale analysis.

The characteristic amount calculation unit 102 extracts, per cell, images of cells included in the cell image acquired in Step S10 (Step S20). The characteristic amount calculation unit 102 performs image processing using a known method on the cell image to extract the images of the cells. In the example, the characteristic amount calculation unit 102 performs contour extraction or pattern matching on the image to extract the images of the cells.

Next, the characteristic amount calculation unit 102 determines types of the cells, with respect to the images of the cells, which are extracted in Step S20 (Step S30). The characteristic amount calculation unit 102 further determines constituent elements of the cells included in the images extracted in Step S20, based on a result of the determination in Step S30 (Step S40). Constituent elements of cells include cell organelles (organelles), such as cell nuclei, lysosomes, Golgi bodies, and mitochondria, and proteins constituting the organelles. Types of cells are determined in Step S30. However, types of cells may not be determined. In this case, when a type of a cell to be introduced is determined in advance, the information may be used. Obviously, a type of a cell may not be specified.

Next, the characteristic amount calculation unit 102 calculates characteristic amounts on the images per constituent element of the cells, which are determined in Step S40 (Step S50). The characteristic amounts include pixel luminance values, areas of regions in the images, and variance values of pixel luminance, for example. Characteristic amounts vary in a plurality of types in accordance with constituent elements of a cell. As an example, characteristic amounts on an image of a cell nucleus include a total intranuclear luminance value and an area of the nucleus, for example. Characteristic amounts on an image of a cytoplasm include a total intracytoplasmic luminance value and an area of the cytoplasm, for example. Characteristic amounts on an image of all cells include a total intracell luminance value and an area of the cells, for example. Characteristic amounts on an image of a mitochondrion include a fragmentation rate. The characteristic amount calculation unit 102 may regularize a result into values ranging from 0 (zero) to 1 to calculate characteristic amounts, for example.

The characteristic amount calculation unit 102 may calculate characteristic amounts based on information on conditions used in an experiment performed on cells associated with a cell image. For example, for a cell image captured when cells are reacted with an antibody, the characteristic amount calculation unit 102 may calculate characteristic amounts specific to cells reacted with the antibody. For a cell image captured when cells are stained or cells are added with a fluorescent protein, the characteristic amount calculation unit 102 may calculate characteristic amounts specific to stained cells or cells added with the fluorescent protein.

In the above described cases, the storage unit 200 may include an experimental condition storage unit 202. The experimental condition storage unit 202 is configured to store, per cell image, information on conditions used in an experiment performed on cells associated with a cell image.

The characteristic amount calculation unit 102 supplies the characteristic amounts calculated in Step S50 to the noise component elimination unit 103.

The noise component elimination unit 103 eliminates noise components from the characteristic amounts calculated in Step S50 (Step S60). Specifically, the noise component elimination unit 103 acquires information indicative of a normal range or an abnormal range for each of the characteristic amounts. The information indicative of the normal range or the abnormal range for each of the characteristic amounts is determined in advance based on characteristics of cells to be captured in a cell image. For example, for characteristic amounts on an image of a cell nucleus, the normal range for a total intranuclear luminance value is specified based on characteristics of an image of the cell nucleus. When one of the calculated characteristic amounts does not fall within the normal range, the noise component elimination unit 103 eliminates the one of the characteristic amounts as a noise component. When characteristic amounts are to be eliminated as noise components, the noise component elimination unit 103 eliminates the characteristic amounts as the noise components per cell. Specifically, a plurality of characteristic amounts may be calculated for a cell. For example, a total intracell luminance value, a total intranuclear luminance value, and an area of a nucleus may be calculated as characteristic amounts of a cell. In this case, when a total intracell luminance value is to be eliminated as a noise component for a cell, the noise component elimination unit 103 also eliminates a total intranuclear luminance value and an area of a nucleus of the cell. In other words, even when at least one characteristic amount among a plurality of characteristic amounts calculated for a cell does not fall within the normal range, the noise component elimination unit 103 further eliminates the other characteristic amounts of the cell.

That is, the noise component elimination unit 103 eliminates noise components per cell captured in a cell image from the characteristic amounts supplied to the correlation extraction unit 104, based on information indicative of the characteristics of the cells captured in the cell image. With this configuration, when a characteristic amount with a relatively low degree of confidence is present, the noise component elimination unit 103 can eliminate the characteristic amount per cell. In other words, with the noise component elimination unit 103, a degree of confidence on a characteristic amount can be improved.

When a calculated characteristic amount falls within the normal range, the noise component elimination unit 103 supplies the characteristic amount to the correlation extraction unit 104. The noise component elimination unit 103 is not an essential constituent element, and can be omitted depending on how cell images are captured or how characteristic amounts are calculated.

The correlation extraction unit 104 uses sparse estimation to extract specific correlations from among a plurality of correlations among the characteristic amounts calculated by the characteristic amount calculation unit 102, based on likelihood of the characteristic amounts (Step S70). A process performed by the correlation extraction unit 104 will now be described more specifically.

In Step S60, the correlation extraction unit 104 acquires characteristic amounts from which noise components are eliminated. The characteristic amounts are calculated per cell by the characteristic amount calculation unit 102 in Step S50. A result of calculation performed by the characteristic amount calculation unit 102 on characteristic amounts of a protein will now be described with reference to FIG. 4.

Figure 4:
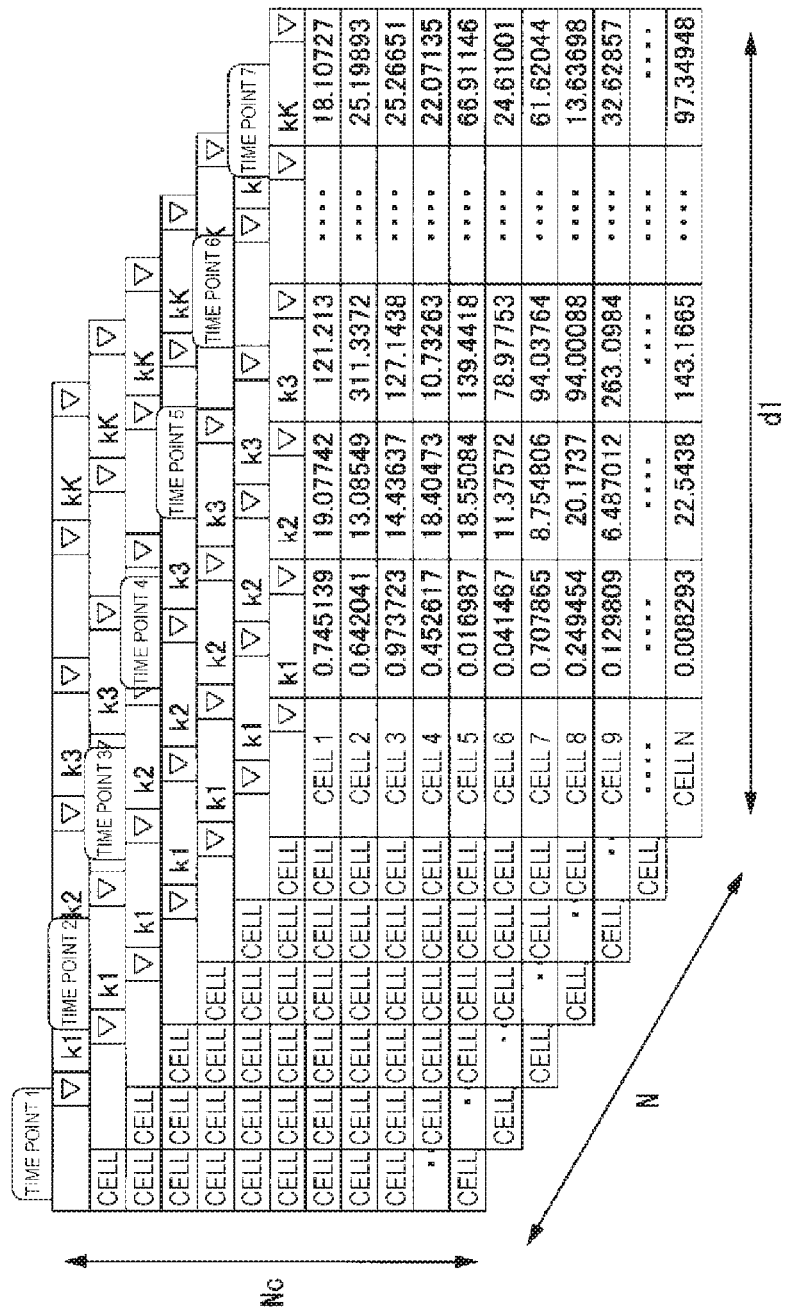
FIG. 4 is a schematic view illustrating an example of a result of calculation of characteristic amounts performed by a characteristic amount calculation unit according to the present embodiment.

FIG. 4 is a schematic view illustrating an example of a result of calculation of characteristic amounts performed by the characteristic amount calculation unit 102 according to the present embodiment. For protein 1, the characteristic amount calculation unit 102 calculates a plurality of characteristic amounts per cell and per time point. In this example, the characteristic amount calculation unit 102 calculates characteristic amounts for an N number of cells ranging from cell 1 to cell N. In this example, the characteristic amount calculation unit 102 calculates the characteristic amounts at seven time points ranging from time point 1 to time point 7. In this example, the characteristic amount calculation unit 102 calculates a K number of types of the characteristic amounts ranging from characteristic amount k1 to characteristic amount kK. In other words, in this example, the characteristic amount calculation unit 102 calculates the characteristic amounts in three axes directions. An axis in a cell direction will be hereinafter referred to as an axis Nc. An axis in a time direction will be hereinafter referred to as an axis N. An axis in a characteristic amount direction will be hereinafter referred to as an axis d1.

The K number of types of the characteristic amounts ranging from characteristic amount k1 to characteristic amount kK denotes a combination of the characteristic amounts with respect to protein 1. For proteins other than protein 1 or for constituent elements of cells other than constituent elements of cells of protein 1, types and combinations of characteristic amounts may differ.

Figure 5:
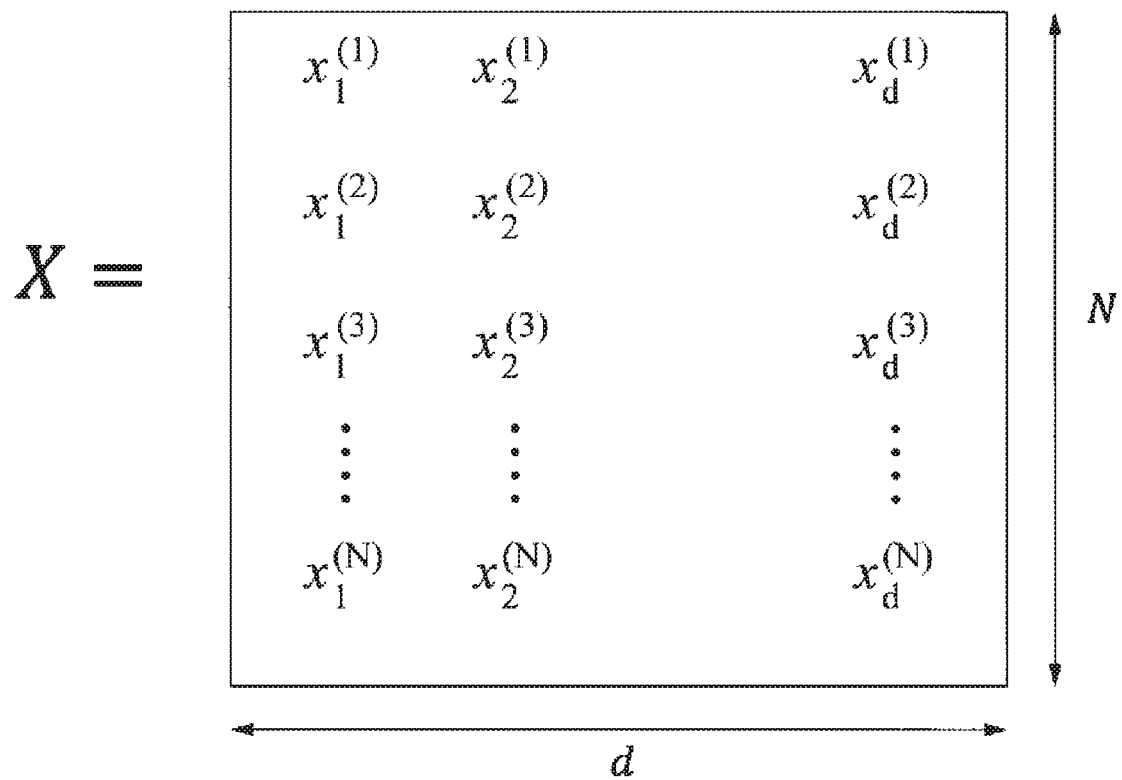
FIG. 5 is a drawing illustrating an example of a matrix of characteristic amounts per cell, according to the present embodiment.

FIG. 5 is a view illustrating an example of a matrix X of characteristic amounts per cell, according to the present embodiment. Characteristic amounts of a cell can be represented by the matrix X having an axis N in a row direction and an axis d in a column direction, as illustrated in FIG. 5. In FIG. 5, elements in the matrix X are illustrated as average values among a cell population. However, such statistics as median values and mode values can be used. Obviously, such statics may be formed into the matrix X of characteristic amounts per cell.

Figure 6:
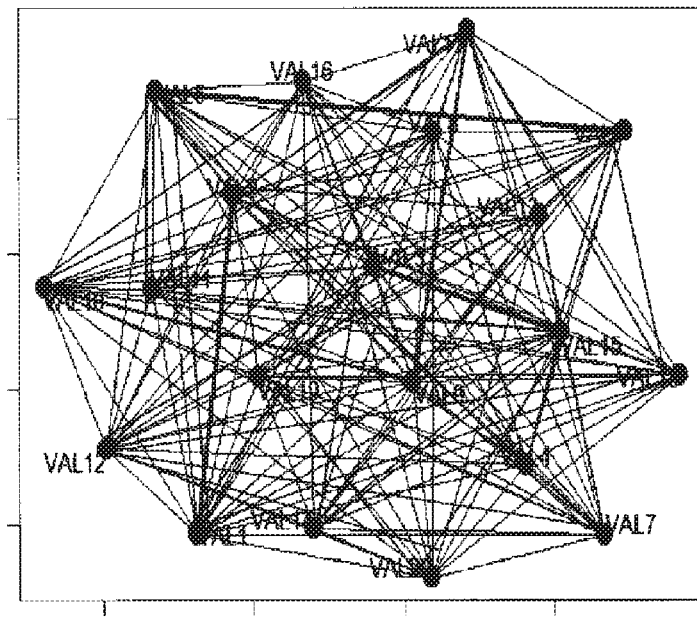
FIG. 6 is a schematic view illustrating an example of correlations among characteristic amounts, according to the present embodiment.

FIG. 6 is a schematic view illustrating an example of correlations among characteristic amounts, according to the present embodiment. The correlation extraction unit 104 extracts specific correlations from among a plurality of correlations among characteristic amounts calculated by the characteristic amount calculation unit 102.

Figure 7:
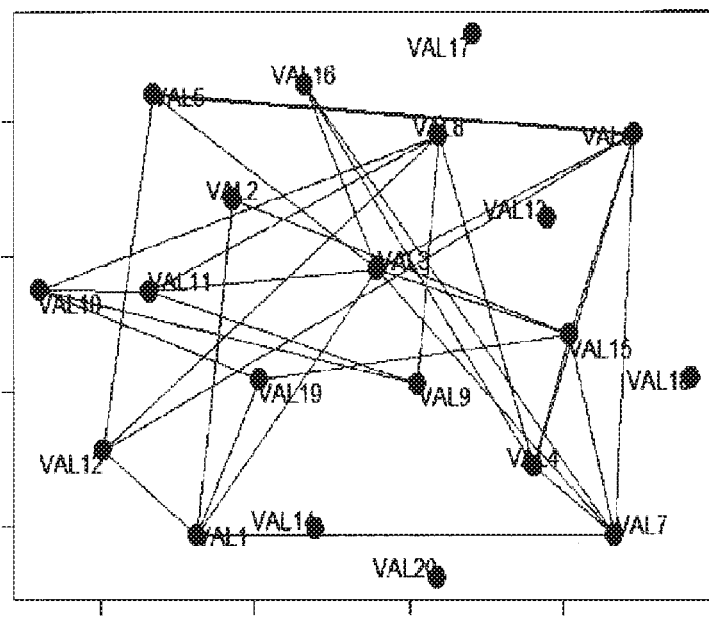
FIG. 7 is a schematic view illustrating an example of specific correlations, according to the present embodiment.

FIG. 7 is a schematic view illustrating an example of specific correlations according to the present embodiment. A specific correlation denotes a correlation selected through mathematical computation from among a plurality of correlations among characteristic amounts. A number of specific correlations is less than a number of correlations among characteristic amounts before the correlation extraction unit 104 performs an extraction. In other words, the correlation extraction unit 104 makes a number of correlations among characteristic amounts sparse. For correlations among characteristic amounts, the correlation extraction unit 104 uses sparse estimation to make a number of the correlations among the characteristic amounts sparse. An example of sparse estimation performed by the correlation extraction unit 104 will now be described.

Likelihood based on a Gaussian model used for sparse estimation by the correlation extraction unit 104 is illustrated in Equation (1).

[Equation 1]

$$\hat{\Lambda} = \underset{\Lambda}{\mathrm{argmax}}[\log \det \Lambda - tr(S\Lambda) - \phi(\Lambda)] \quad (1)$$

$\hat{\Lambda}$: Estimated Precision Matrix $S$: Sample Variance-Covariance Matrix In Equation (1), the term of "$\varphi(\Lambda)$" represents a regularization term. For a function form of the regularization term, various forms are available in accordance with an attribute of a correlation desired to be extracted. In particular, under an assumption of a Gaussian model, it is known that a precision matrix having sparse components can be acquired when an L1 regularization term is added, as illustrated in Equation (2). The symbol $\lambda$ in Equation (2) denotes strength of regularization. The symbol $\lambda$ has a characteristic where the larger the value, the more sparse the components in a precision matrix.

[Equation 2]

$$\phi(\Lambda) \equiv \|\Lambda\|_1 \quad (2)$$

For example, by setting a regularization term as illustrated in Equation (3), a sparse partial matrix can be acquired.

[Equation 3]

$$\phi(\Lambda) \equiv \sum_{i \neq i'} w_{ii'} |\Lambda_{ii'}| \quad (3)$$

$$w_{ii'} = \begin{cases} \lambda_k & \text{if } i \in C_k \\ \infty & \text{if } i \in C_k, i' \in C_k, k' \neq k \end{cases}$$

Sparse estimation based on Graphical Lasso

An example of sparse estimation when a regularization term is a function form based on Graphical Lasso will now be described. Graphical Lasso refers to an efficient algorithm used to estimate a precision matrix from a Gaussian model with an L1 regularization. For example, see "Sparse inverse covariance estimation with the graphical lasso" in Biostatistics (2008), 9, 3 432-441, written by JEROME FRIEDMAN, TREVOR HASTIE, and ROBERT TIBSHIRANI.

First, likelihood with the L1 regularization based on a Gaussian model in Equation (1) adopted with Equation (2) is differentiated with a precision matrix.

[Equation 4]

$$L(\Lambda) \equiv \log\det(\Lambda) - tr(S\Lambda) - \lambda|\Lambda|_1 \quad (4)$$

$$\frac{\partial L}{\partial \Lambda} = \Lambda^{-1} - S - \lambda, (|\Lambda| > 0), \ \Lambda^{-1} - S - \lambda, (|\Lambda| < 0),$$

undefined $(|\Lambda| = 0)$

Next, under a condition that the precision matrix is a positive definite matrix, a diagonal component is acquired, as illustrated in Equation (5).

[Equation 5]

$$[\Lambda^{-1}]_{ii} = [\Sigma]_{ii} = [S]_{ii} + \lambda \equiv \sigma \quad (5)$$

Next, by focusing on a specific variable i, and by dividing a variance-covariance matrix, a precision matrix, and a sample covariance matrix into block matrices, as illustrated in Equation (6), Equation (4) can be modified, as illustrated in Equation (7).

[Equation 6]

$$\Sigma = \Lambda^{-1} = \begin{pmatrix} W & w \\ w^t & \sigma \end{pmatrix}, \ \Lambda = \begin{pmatrix} L & l \\ l^t & L_{ii} \end{pmatrix}, \ S = \begin{pmatrix} S^{\setminus i} & s \\ s^t & s_{ii} \end{pmatrix} \quad (6)$$

[Equation 7]

$$\frac{\partial L}{\partial \Lambda} = w - s - \lambda \mathrm{sgn}(l), \ \beta \equiv W^{-1}w \quad (7)$$

[Equation 8]

$$\beta^* = \mathrm{argmin}_\beta [L'(\beta)] \quad (8)$$

$$L'(\beta) \equiv \frac{1}{2}\beta^t W \beta - \beta^t s + \rho|\beta|$$

Equation (7) can arrive back to Equation (8) representing an optimization problem of an ordinary Lasso regression, and can be acquired with an existing solver, for example.

[Equation 9]

$$\frac{\partial L'}{\partial \beta^*} = \quad (9)$$

Upon an optimum solution $\beta^*$ (beta asterisk) for Equation (8) satisfying a condition of Equation (9) is acquired, components of the block matrices represented by Equation (6) can be acquired by using Equation (11) and Equation (12), both of which can be derived from Equation (6), Equation (7), and Equation (10). Where, the symbol I in Equation (10) denotes a unit matrix.

[Equation 10]

$$\Sigma\Lambda = I, \ \beta \equiv W^{-1}w \quad (10)$$

[Equation 11]

$$l = -\frac{\beta^*}{\sigma - \beta^{*t}W\beta^*}, \ \Lambda_{ii} = -\frac{1}{\sigma - \beta^{*t}W\beta^*} \quad (11)$$

[Equation 12]

$$w = -\frac{Wl}{\Lambda_{ii}} \quad (12)$$

Computations are repeated by Equation (5) to Equation (12), described above, and by switching rows and columns.

As described above, the image processing apparatus 10 causes the correlation extraction unit 104 to perform sparse estimation to make a number of correlations among characteristic amounts sparse. Therefore, with the image processing apparatus 10, an analysis can be performed with a reduced number of correlations among characteristic amounts. In other words, with the image processing apparatus 10, a computation amount for analyses of correlations among characteristic amounts can be reduced. A number of correlations among characteristic amounts can be reduced by utilizing likelihood as an index. Therefore, analysis failures, which occur when a computation amount for analyses of correlations among characteristic amounts is intentionally reduced by a person, for example, can be reduced. To acquire correlations among characteristic amounts, the characteristic amounts are acquired from an image of cells. For characteristic amounts, other than information acquired from the images, information, such as luminosity information directly derived from the images, is further used. For example, a location (nucleus, nuclear membrane, or cytoplasm) in a cell in luminosity information is estimated from a shape of an image. For example, a location (nucleus, nuclear membrane, or cytoplasm) of a stained portion (portion having luminosity information) in a stained cell is estimated. As a result, a computation amount becomes greater for acquiring correlations among characteristic amounts by using, in addition to information directly derived from image information, information estimated from the image information. Therefore, with the correlation extraction unit 104 configured to perform sparse estimation to make a number of correlations among characteristic amounts sparse, a computation amount can be prevented, as much as possible, from becoming greater.

For example, a case when acquiring correlations in a cell will be described. When acquiring correlations in a cell, a plurality of cells may be acquired from an image, for example. In the plurality of cells, correlations among the cells can thus be acquired. In this case, acquiring correlations in each of a plurality of cells can acquire correlations among the plurality of cells, compared with a case when acquiring correlations in a single cell. As a result of acquiring correlations, highly precise pathways of signal transmissions can be calculated, for example. When acquiring correlations in each of a plurality of cells for higher precision, a computation amount for acquiring correlations becomes greater. In this case, reducing a computation amount by utilizing likelihood as an index can reduce analysis failures.

For example, a case when acquiring correlations among cells will be described. When acquiring correlations among cells, a plurality of cells may be acquired from an image, for example. In the plurality of cells, correlations among the cells can thus be acquired. In this case, a predetermined cell may correlate to a plurality of cells, as well as cells other than the predetermined cell may also correlate to the plurality of cells. In this case, acquiring correlations among the cells can improve precision of pathways of signal transmissions to be calculated among the cells, as a result of acquiring correlations, for example. When acquiring correlations in each of a plurality of cells for higher precision, a computation amount for acquiring correlations becomes greater. In this case, reducing a computation amount by utilizing likelihood as an index can reduce analysis failures.

For example, for characteristic amounts calculated by the characteristic amount calculation unit 102, when cells receive signals from outside the cells, and when acquiring signal transmissions in the cells as correlations, types of proteins involving the signal transmissions in the cells may be extracted as characteristic amounts. That is, types of substances involving signal transmissions in cells may be extracted, as well as changes in shape of cells as a result of transmissions of signals in the cells may be extracted, for example. For identifying substances involving signal transmissions in a cell, nuclear magnetic resonance (NMR) may be used, as well as a method for analogizing a target of interaction from a stain solution to be used may be used, for example.

Determination of Regularization Parameter

Next, determination of a regularization parameter in sparse estimation performed by the correlation extraction unit 104 will now be described. Sparse estimation is advantageous because of its relatively highly flexible models, and its capability of adjusting a model for easy interpretation for humans and computers. On the other hand, a problem observed in sparse estimation is that a unique model cannot be determined due to its dependency on regularization parameter. Procedures for determining a regularization parameter to solve this problem are as follows. The procedures for determining a parameter includes, as examples, a procedure for determining a parameter through cross-validation and a procedure for determining a parameter by utilizing biological knowledge. The procedure for determining a parameter through cross-validation will now be described.

Estimation of λ Through Cross-Validation

Figure 8:
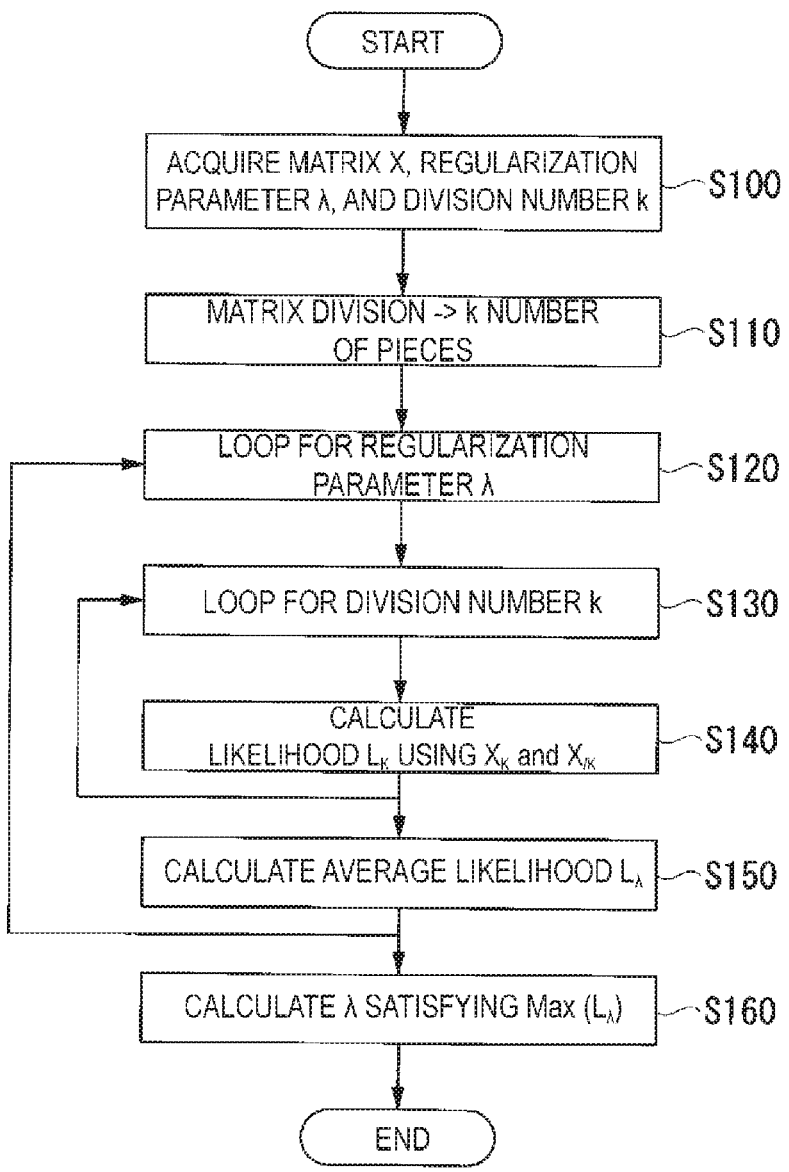
FIG. 8 is a flowchart illustrating an example of a procedure for cross-validation, performed by a correlation extraction unit according to the present embodiment.

FIG. 8 is a flowchart illustrating an example of a procedure for cross-validation, performed by the correlation extraction unit 104 according to the present embodiment.

The correlation extraction unit 104 acquires a matrix X, a regularization parameter λ, and a division number K (Step S100). The correlation extraction unit 104 divides the matrix X based on the division number K acquired in Step S100 (Step S110).

Next, the correlation extraction unit 104 processes double loops: a loop for regularization parameter λ (Step S120) and a loop for division number K (Step S130). In the loop for division number K, the correlation extraction unit 104 calculates likelihood Lk by using a matrix Xk and a matrix X/k (Step S140). In the loop for regularization parameter λ, the correlation extraction unit 104 calculates average likelihood Lk for the likelihood Lk of a regularization parameter λ (Step S150). A procedure for calculating the average likelihood U performed by the correlation extraction unit 104 will be described in detail with reference to FIG. 9.

Figure 9:
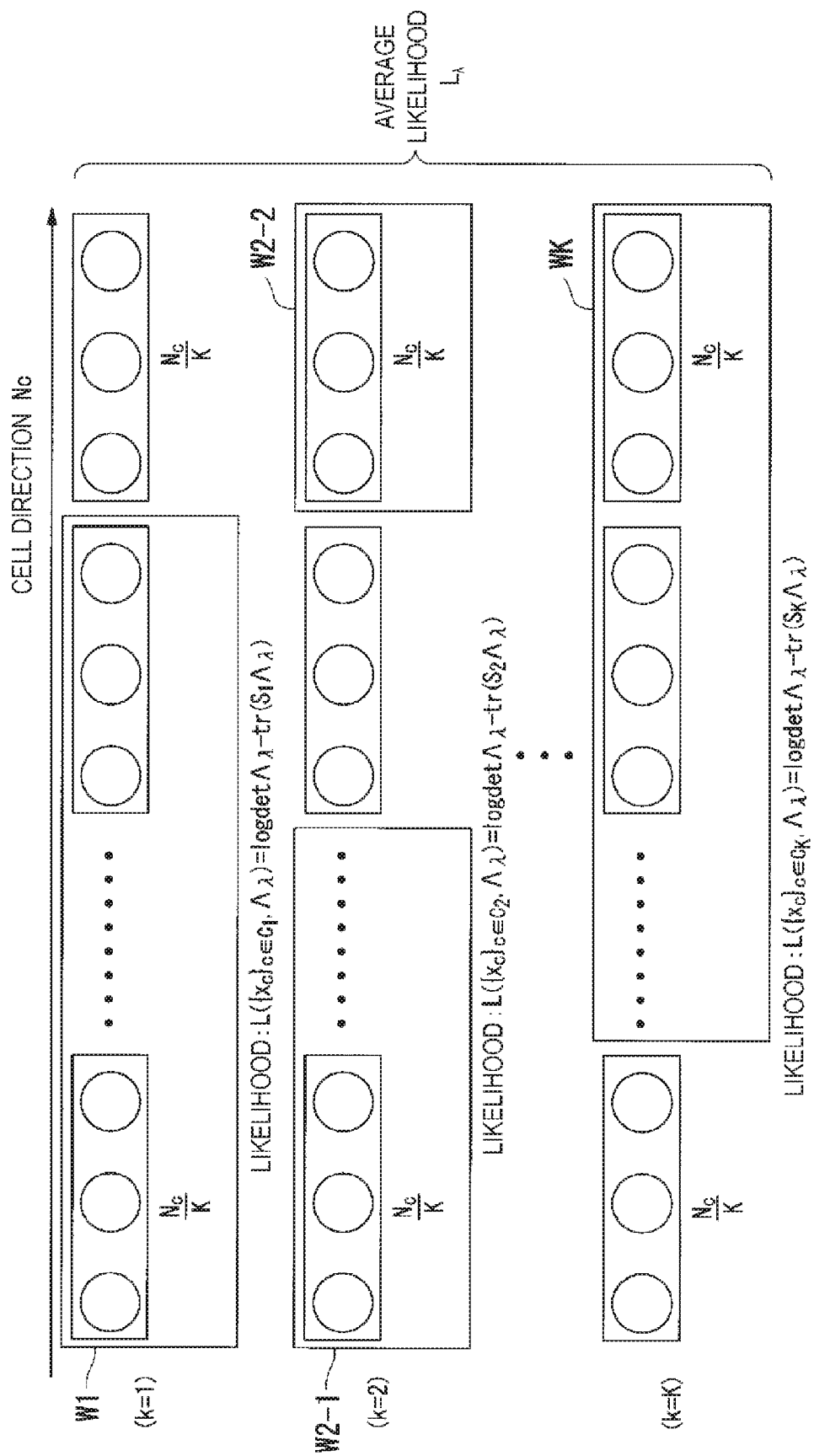
FIG. 9 is a schematic view illustrating an example of a procedure for calculating average likelihood, performed by the correlation extraction unit according to the present embodiment.

FIG. 9 is a schematic view illustrating an example of a procedure for calculating the average likelihood Lλ, performed by the correlation extraction unit 104 according to the present embodiment. In the loop for division number K, described above, the correlation extraction unit 104 divides the matrix X into a K number of pieces in the cell direction Nc. The correlation extraction unit 104 calculates the likelihood Lk with respect to the matrix X divided into the K number of pieces.

Specifically, the correlation extraction unit 104 calculates likelihood L1 for elements included in a calculation frame W1 illustrated in FIG. 9 (k=1). For a regularization parameter λ, the correlation extraction unit 104 further calculates likelihood L2 for elements included in a calculation frame W2-1 and a calculation frame W2-2 illustrated in FIG. 9 (k=2). The correlation extraction unit 104 further calculates likelihood LK for elements included in a calculation frame WK illustrated in FIG. 9 (k=K). In other words, for a regularization parameter λ, the correlation extraction unit 104 calculates the likelihood Lk ranging from k=1 to k=K, respectively. For the likelihood Lk calculated per the regularization parameter λ, the correlation extraction unit 104 calculates the average likelihood Lλ by using Equation (13).

[Equation 13]

$$L_\lambda = \frac{1}{K} \sum_k^K L(\{x_c\}_{c \in C_k}, \Lambda_\lambda) \quad (13)$$

Next, the correlation extraction unit 104 calculates, as the regularization parameter λ for a calculation target, the regularization parameter λ with the average likelihood Lk indicating a maximum value Max (Lλ) (Step S160), and then ends the calculation of the regularization parameter λ. An example of a procedure for calculating the regularization parameter λ performed by the correlation extraction unit 104 will now be described.

Figure 10:
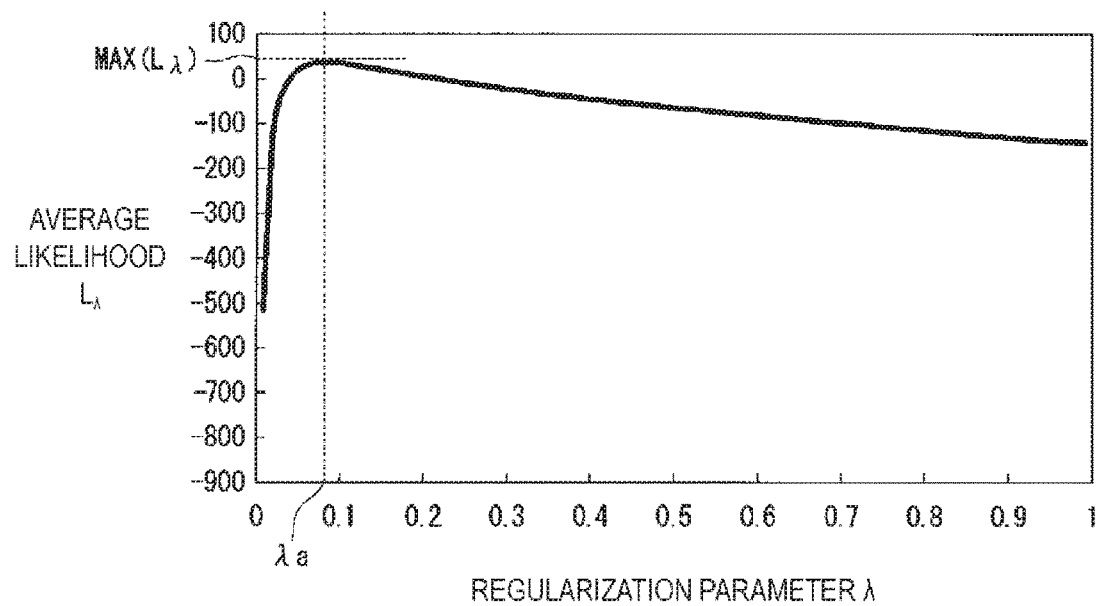
FIG. 10 is a graph illustrating an example of a relationship between average likelihood and a regularization parameter, according to the present embodiment.

In this example, the correlation extraction unit 104 calculates the likelihood Lλ when the regularization parameter λ is changed from 0 to 1. Specifically, the correlation extraction unit 104 selects a value from 0 to 1 and substitutes the value for the regularization parameter λ to calculate the likelihood Lk illustrated in FIG. 9. The correlation extraction unit 104 calculates an average of the likelihood Lk, i.e., the average likelihood Lλ to generate a correspondence relationship between the regularization parameter λ, and the average likelihood Lλ. FIG. 10 illustrates the correspondence relationship between the regularization parameter λ and the average likelihood Lλ, which is generated by the correlation extraction unit 104.

FIG. 10 is a graph illustrating an example of the relationship between the average likelihood Lk and the regularization parameter λ, according to the present embodiment. In the example illustrated in FIG. 10, the average likelihood Lλ shows a maximum value at a regularization parameter λa. In this case, the correlation extraction unit 104 calculates the regularization parameter λa as the regularization parameter λ for a calculation target.

In Step S110 described above, when the correlation extraction unit 104 divides the matrix X with the division number K into a K number of pieces, the correlation extraction unit 104 divides the matrix X in the cell direction Nc. In other words, the correlation extraction unit 104 acquires likelihood L of characteristic amounts based on a number of cells captured in a cell image to extract specific correlations. The correlation extraction unit 104 can further divide the matrix X in the time direction N. However, to allow the correlation extraction unit 104 to divide the matrix X in the time direction N, a plurality of cell images ranging in the time direction N are required. In other words, to allow the correlation extraction unit 104 to divide the matrix X in the time direction N, a plurality of cell images captured at different time points are required. On the other hand, to allow the correlation extraction unit 104 to divide the matrix X in the cell direction Nc, a plurality of cell images captured at different time points are not required. In other words, even when a plurality of cell images captured at different time points are not available, the correlation extraction unit 104 according to the present embodiment can calculate the regularization parameter λ from a single cell image, for example.

Biological interpretation on result of sparse estimation

Next, biological interpretation on a result of sparse estimation performed by the correlation extraction unit 104 will now be described with reference to FIGS. 11 to 13. Biological interpretation on a result of sparse estimation performed by the correlation extraction unit 104 can be added, based on biological information. This example describes that biological information is stored in advance in the storage unit 200. However, the present invention is not limited to this example. Biological information may be supplied from outside the microscope observation system 1 via a network or a portable storage medium. Biological information includes an intracell constituent element annotation database and a characteristic amount annotation database, for example. Intracell constituent elements denote elements constituting a cell. Elements constituting a cell include proteins, genes, and chemical compounds, for example. A specific example of a procedure for biological interpretation on a result of sparse estimation performed by the correlation extraction unit 104 will now be described.

Figure 11:
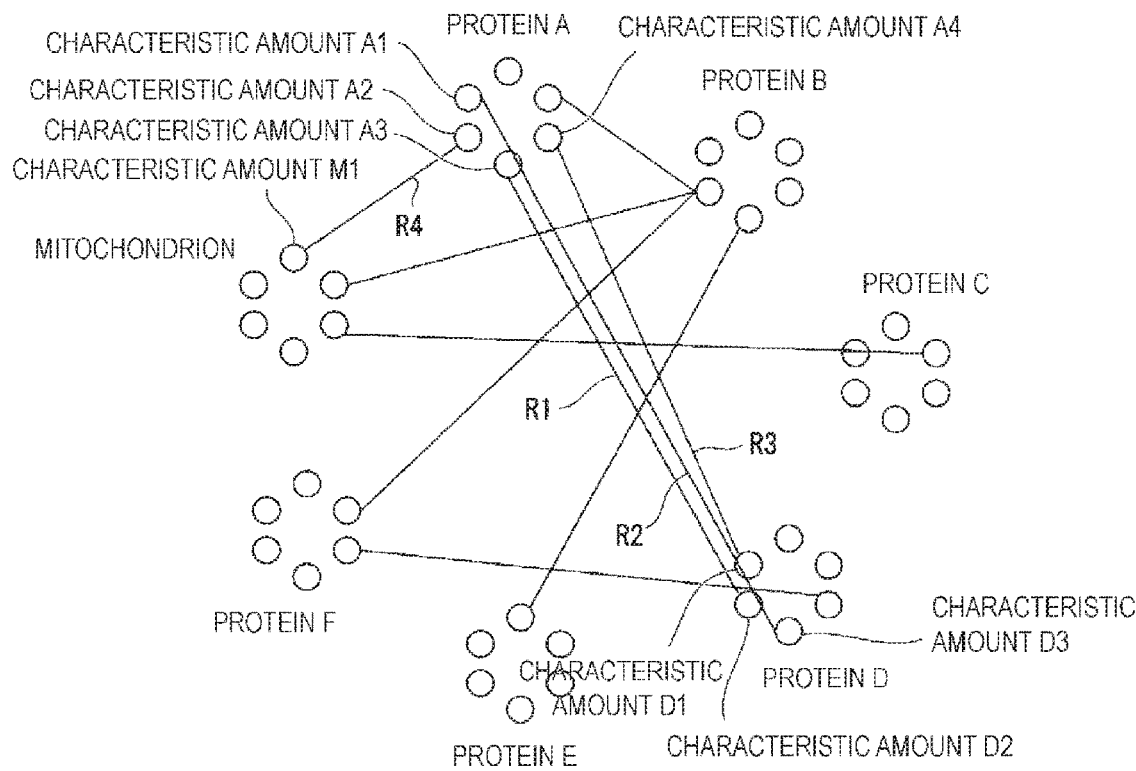
FIG. 11 is a schematic view illustrating an example of a result of extraction of correlations among characteristic amounts, performed by the correlation extraction unit according to the present embodiment.

FIG. 11 is a schematic view illustrating an example of a result of extraction of correlations among characteristic amounts, performed by the correlation extraction unit 104 according to the present embodiment. In the example, the correlation extraction unit 104 extracts correlations among characteristic amounts of a mitochondrion and six types of proteins ranging from protein A to protein F.

In this example, a cell image is captured with cells including the mitochondrion and protein A to protein F. The characteristic amount calculation unit 102 calculates characteristic amounts on types corresponding to the mitochondrion and protein A to protein F. That is, the characteristic amount calculation unit 102 calculates characteristic amounts on types corresponding to types of intracell constituent elements of cells captured in a cell image, among a plurality of types of characteristic amounts.

Specifically, the correlation extraction unit 104 extracts, from among characteristic amounts of protein A and characteristic amounts of protein D, three types of correlations: correlation R1, correlation R2, and correlation R3. Correlation R1 represents a correlation between characteristic amount A3 of protein A and characteristic amount D2 of protein D. Correlation R2 represents a correlation between characteristic amount A1 of protein A and characteristic amount D3 of protein D. Correlation R3 represents a correlation between characteristic amount A4 of protein A and characteristic amount D1 of protein D. For example, characteristic amount A1 represents a value of variance in an image of protein A. Characteristic amount D3 represents a value of luminance in an image of protein D.

The correlation extraction unit 104 extracts correlation R4 between one of the characteristic amounts of protein A and one of characteristic amounts of the mitochondrion. Correlation R4 represents a correlation between characteristic amount A2 of protein A and characteristic amount M1 of the mitochondrion. Characteristic amount A2 represents a ratio of a total intranuclear luminance value with respect to a total intracell luminance value of the image of protein A, for example. For example, characteristic amount M1 represents a fragmentation rate of the mitochondrion, indicated by the image of the mitochondria.

FIG. 12 is a table illustrating an example of an intracell constituent element annotation database according to the present embodiment. In the intracell constituent element annotation database, types of intracell constituent elements and functions of the intracell constituent elements are associated with each other. In an example of the present embodiment, the intracell constituent element annotation database is stored in advance in the storage unit 200. Specifically, in the intracell constituent element annotation database, the type "protein A" is associated with the function "transcription factor (activation)". In the intracell constituent element annotation database, the type "protein B" is associated with the function "kinase".

FIG. 13 is a table illustrating an example of a characteristic amount annotation database according to the present embodiment. In the characteristic amount annotation database, NW elements, characteristic amounts, directions of changes in the characteristic amounts, and information indicative of biological implication are associated with each other. In the example of the present embodiment, the characteristic amount annotation database is stored in advance in the storage unit 200. Specifically, in the characteristic amount annotation database, the NW element "transcription factor (activation)", the characteristic amount "total intranuclear luminance value/total intracell luminance value", the change in characteristic amount "UP", and the biological implication "transactivation" are associated with each other. In the characteristic amount annotation database, the NW element "mitochondrion", the characteristic amount "fragmentation rate", the change in characteristic amount "UP", and the biological implication "division activation, rise in oxidative stress, and increase in mitophagy" are associated with each other. The characteristic amount annotation database is merely a specific example for the type storage unit 201 included in the storage unit 200. In other words, the type storage unit 201 is stored with types of intracell constituent elements of cells captured in a cell image, and types of characteristic amounts, which are respectively associated with each other.

When extracted correlation R4 representing a correlation between the ratio of the total intranuclear luminance value with respect to the total intracell luminance value of the image of protein A and the fragmentation rate of the mitochondrion is higher, biological interpretation can be performed as described below.

That is, based on the intracell constituent element annotation database, it is determined that the function of protein A is "transcription factor (activation)". Based on the characteristic amount annotation database, when the characteristic amount "total intranuclear luminance value/total intracell luminance value" associated with "transcription factor (activation)" indicates the change in characteristic amount "UP", it can be determined that the biological implication is "transactivation". Based on the characteristic amount annotation database, when the characteristic amount "fragmentation rate" associated with "mitochondrion" indicates the change in characteristic amount "UP", it can be determined that the biological implication is "division activation, raise in oxidative stress, and increase in mitophagy".

Based on the results of the determinations, biological interpretation on correlation R4 described below can be added. That is, (1) Protein A activates transcription of proteins related to mitochondrial division. (2) Protein A activates transcription of proteins promoting mitophagy.

As described above, with the image processing apparatus 10, based on biological information and a result of extraction of correlations among characteristic amounts of cells, a suggestion can be added to biological interpretation on the correlations.

From characteristic amounts of cells, which are used to acquire correlations, biological information on the characteristic amounts is created. That is, biological information on the characteristic amounts of the cells, which are used to acquire the correlations, is created. In this way, biological interpretation on extracted correlations can be performed.

Extraction of characteristics of characteristic amount network using result of sparse estimation By utilizing a result of sparse estimation performed by the correlation extraction unit 104, elements of a characteristic amount network can be extracted. A characteristic amount network represents a network of correlations among characteristic amounts. Elements of a characteristic amount network include node, edge, sub-graph (cluster), and link. Characteristics of a characteristic amount network include whether a hub is present and whether a cluster is present, for example. For example, whether a node has a hub can be determined based on a value of a partial correlation matrix. A hub denotes a characteristic amount having a relatively greater number of correlations with other characteristic amounts.

When a hub is present in a node, it is conceivable that a characteristic amount representing the hub or the node including the hub has a biologically important implication. Therefore, finding presence of a hub may lead to finding an important protein and an important characteristic amount. In other words, utilizing a result of sparse estimation performed by the correlation extraction unit 104 can contribute to finding of an important protein and an important characteristic amount.

Therefore, the correlation extraction unit 104 can use sparse estimation to calculate a characteristic amount network, and to identify one or more elements from among a plurality of elements constituting the characteristic amount network. In this way, elements to be first taken into account when acquiring correlations can be extracted. When elements are extracted, the elements can further be taken into account when acquiring other correlations.

Obviously, the correlation extraction unit 104 can use sparse estimation to calculate a characteristic amount network, and to identify one or more groups of elements from among a plurality of groups of elements constituting the characteristic amount network. A group of elements may be a plurality of proteins each having an identical secondary structure, for example.

Detection of change among characteristic amount networks

By utilizing a result of sparse estimation performed by the correlation extraction unit 104, a change among a plurality of characteristic amount networks can be detected.

FIG. 14 is a drawing illustrating an example of a model for comparing characteristic amount networks, according to the present embodiment. Characteristic amount networks can be mutually compared per particle size ranging from micro to macro. Specifically, based on a change in relationship, detection of a change in edge particle size can be performed. In detection of a change in edge particle size, a d(d−1)/d number of scores are used. Based on a change in variable, detection of a change in node particle size can be performed. In detection of a change in node particle size, a d number of scores are used. Based on a change in EGONET, detection of a change in cluster particle size can be performed. In detection of a change in cluster particle size, a d number of scores are used. Based on a change in network, detection of a change in network particle size can be performed. In detection of a change in network particle size, one score is used.

Detection of a change in node particle size is performed through a probabilistic neighborhood method, for example. Detection of a change in node particle size through the probabilistic neighborhood method can be performed by calculating a neighbor probability between an i-th element and a j-th element in a dissimilarity matrix, and then by scoring the neighbor probability. By arranging scores on indexes for proteins per protein and per index, changes in score can be graphically shown. For example, see Proceedings of the Seventh IEEE International Conference on Data Mining (ICDM), Oct. 28-31, 2007, pp 523-528, written by Tsuyoshi Ide, Spiros Papadimitriou, and Michail Vlachos.

Detection of a change in cluster particle size is performed through an EGONET. EGONET refers to a view in which, in a characteristic amount network including nodes and edges, each of the nodes (Ego) is focused on to illustrate a relationship among the node being focused on, other nodes related to the node being focused on, and edges spread from the nodes. With an EGONET, edges with respect to a node being focused on can be extracted from all edges included in a characteristic amount network. Therefore, comparing EGONETs with each other is easier than comparing characteristic amount networks each other. This advantageously visualizes a correlation structure around a node being focused on.

A variation to detection of a change in characteristic amount network is a quantitative comparison of two or more characteristic amount networks. For example, a characteristic amount network on cells sampled from tissues of a diseased person and a characteristic amount network on cells sampled from tissues of a healthy person can be compared with each other. In this case, by comparing the characteristic amount networks with each other, a structure of a characteristic amount network specific to the disease can be found. In the present embodiment, the correlation extraction unit 104 uses sparse estimation to derive a characteristic amount network that is sparse and thus is easily interpretable. Therefore, comparison of characteristic amount networks can become easier, compared with a case when no sparse estimation is used.

When comparing characteristic amount networks, network learning through support vector machine (SVM) or random forest, for example, may be used. In network learning, a regularization parameter may be adjusted for improved classification performance.

Identification of proteins having identical function through comparison of characteristic amount networks When protein P1 and protein P2 respectively have an identical function, a difference might not be observed between an edge between protein P1 and protein Pn and an edge between protein P2 and protein Pn. In other words, when protein P1 and protein P2 are regarded as identical proteins, structures of characteristic amount networks are similar to each other. By utilizing this characteristic, proteins having an identical function can be identified. For example, when the correlation extraction unit 104 performs sparse estimation, proteins having an identical function can be identified by extracting a characteristic amount network from which only protein P1 is eliminated and a characteristic amount network from which only protein P2 is eliminated.

Determination of regularization parameter utilizing biological knowledge

Figure 15:
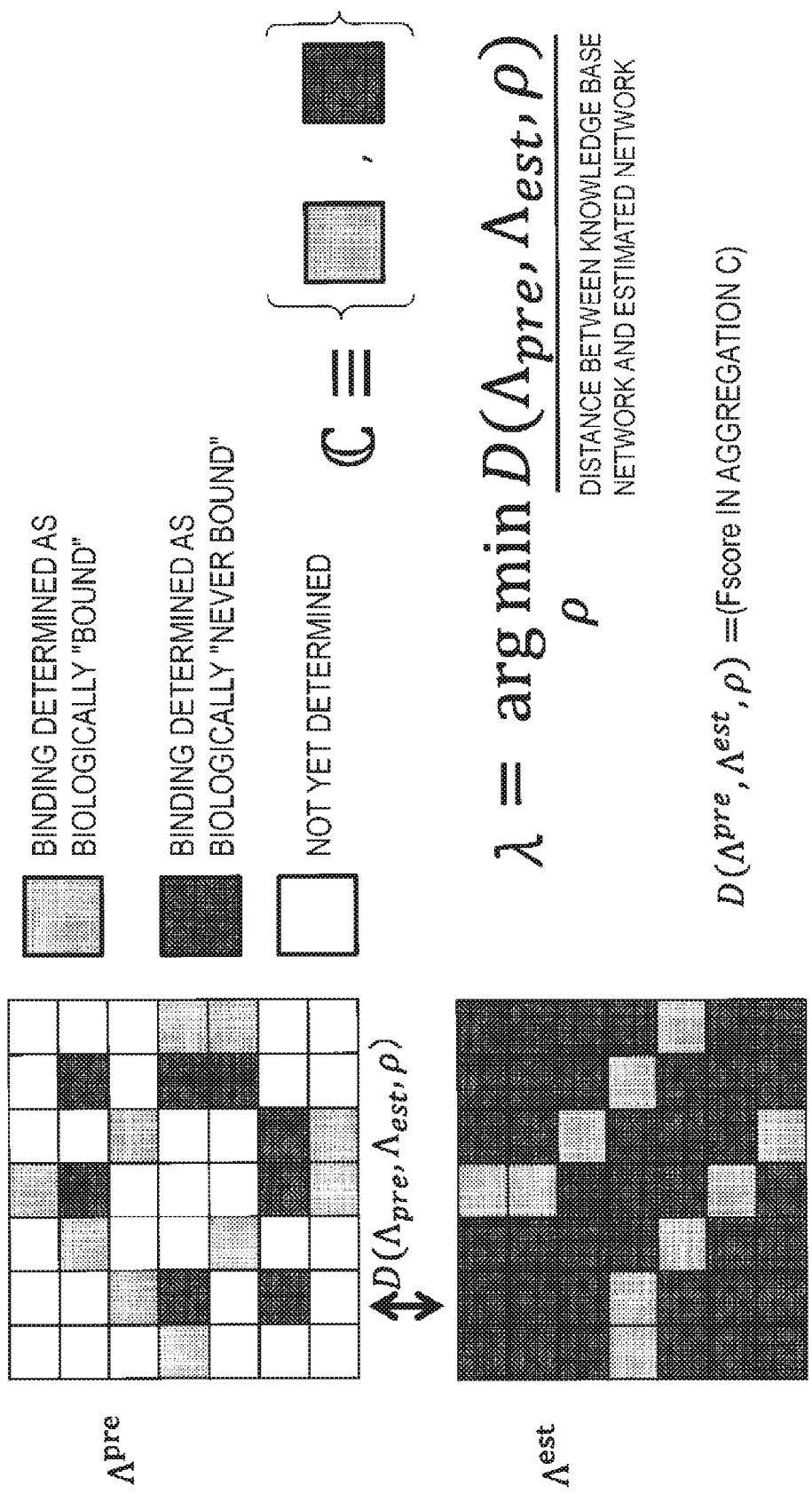
FIG. 15 is a drawing illustrating an example of a procedure for determining a regularization parameter using biological knowledge, according to the present embodiment.

FIG. 15 is a diagram illustrating an example of a procedure for determining a regularization parameter using biological knowledge, according to the present embodiment. In the example, binding of proteins is specified in advance based on biological knowledge. Specifically, based on biological knowledge, between a characteristic amount of a protein and a characteristic amount of another protein, binding determined as "bound" and binding determined as "never bound" are specified in advance as a knowledge database. In the present embodiment, the knowledge database specified in advance may be stored in the storage unit 200.

By calculating a distance between the knowledge database and a characteristic amount network represented by a result of sparse estimation performed by the correlation extraction unit 104, that is, by calculating a Fscore, a regularization parameter λ is determined. Fscore is illustrated as Equation (16) with Precision illustrated in Equation (14) and Recall illustrated in Equation (15). An Fscore depends on a regularization parameter. A value when an estimated network is closest to the knowledge database is taken as a maximum value. A regularization parameter at this time is then adopted. As illustrated in FIG. 15, even when the knowledge database is not enough, that is, components in a matrix are not fully labelled, a range of regularization parameters can be narrowed.

[Equation 14]

$$\text{Precision} = \frac{TP}{TP+FP} \quad (14)$$

[Equation 15]

$$\text{Recall} = \frac{TP}{TP+FN} \quad (15)$$

[Equation 16]

$$Fscore = \frac{2\text{Recall} \cdot \text{Precion}}{\text{Recall} + \text{Precision}} \quad (16)$$

FIG. 16 illustrates a relationship among TP, FP, and FN in Equation (14) and Equation (15).

FIG. 16 is a diagram illustrating a relationship between the knowledge base network and a prediction network, with respect to whether binding is present in a characteristic amount network, according to the present embodiment. The term "Precision" used herein denotes a ratio of actual edges among targets predicted as edges with respect to an element in a characteristic amount network. The term "Recall" used herein denotes a ratio of targets predicted as edges among actual edges with respect to an element in a characteristic amount network.

As described above, the correlation extraction unit 104 may acquire likelihood of characteristic amounts based on information indicative of characteristics of cells captured in a cell image to extract specific correlations.

Correlations extracted with the above described embodiment may be verified as required by using academic documents and databases. When a database is divided into a plurality of pieces, information may be selected as required from the divided pieces of the database. In this case, the divided pieces of the database may be separated by type, such as gene and protein. By combining results of verification based on a plurality of databases, extracted correlations may be verified.

The above-described various processing steps may be realized by recording a program for executing these processing steps of the image processing apparatus 10 in a recording medium that can be read by a computer and causing a computer system to read and execute the program recorded in the recoding medium.

Note that the "computer system" referred to here includes an operating system (OS) and hardware such as a peripheral device. Further, when the "computer system" uses a world wide web (WWW) system, this includes a homepage provision environment (or display environment). Moreover, a "recording medium that can be read by a computer" refers to a portable recording medium such as a flexible disk, a magneto-optical disk, a read-only memory (ROM), a writable non-volatile memory such as a flash memory, or a CD-ROM, or a storage device such as a hard disk that is built into the computer system.

Further, the "recording medium that can be read by a computer" may also include a medium that holds the program for a certain period of time, such as a volatile memory (a Dynamic Random Access Memory (DRAM), for example) built into a computer system that is a server or a client when the program is transmitted over a network such as the Internet or a communication line such as a telephone line. In addition, the above-described program may be transmitted, from the computer system in which the program is stored in a storage device or the like, to another computer system, via a transmission medium or by transmission waves in the transmission medium. Here, the "transmission medium" that transmits the program refers to a medium having a function to transmit information, such as the Internet or another network (communication network), and a communication line such as a telephone line. Further, the above-described program may be a program for realizing a part of the above-described functions. Moreover, the above-described functions may be realized by a combination of this program with a program already recorded in the computer system, namely, by a so-called differential file (differential program).

Above, the embodiments of the present invention are described in detail with reference to the drawings, but a specific configuration is not limited to the embodiments, and designs and the like within the scope of the present invention are included.

REFERENCE SIGNS LIST

1 Microscope observation system
10 Image processing apparatus
20 Microscope apparatus
101 Cell image acquisition unit
102 Characteristic amount calculation unit
103 Noise component elimination unit
104 Correlation extraction uni

The invention claimed is:

1. An image processing apparatus comprising:
   a processor programmed to
      acquire a cell image captured with cells;
      calculate a plurality of types of characteristic amounts on the acquired cell image; and
      extract specific correlations from among a plurality of correlations among the calculated characteristic amounts r, based on a likelihood of the characteristic amounts; and
   a memory configured to store types of the characteristic amounts and either or both of types of the cells and types of the constituent elements of the cells that are captured in the cell image, the types of the characteristic amounts and either or both of the types of the cells and the types of the constituent elements of the cells being associated with each other,
   wherein the processor calculates, from among the plurality of types of the characteristic amounts, types of the characteristic amounts corresponding to types of the cells and types of the constituent elements of the cells that are captured in the cell image.

2. The image processing apparatus according to claim 1, wherein the processor acquires the likelihood of the characteristic amounts based on a number of the cells captured in the cell image to extract the specific correlations.

3. The image processing apparatus according to claim 1, wherein the processor acquires the likelihood of the characteristic amounts based on information indicative of characteristics of the cells captured in the cell image to extract the specific correlations.

4. The image processing apparatus according to claim 1, wherein, with respect to the characteristic amounts used to extract the correlations, the processor extracts a biological interpretation indicated by the extracted correlations, based on biological information on the extracted characteristic amounts.

5. The image processing apparatus according to claim 1, wherein the processor is further programmed to eliminate noise components per cell captured in the cell image from the characteristic amounts supplied to the processor, based on the information indicative of the characteristics of the cells captured in the cell image.

6. The image processing apparatus according to claim 1, wherein the processor calculates the characteristic amounts per constituent element of the cells and/or cell that are captured in the cell image.

7. The image processing apparatus according to claim 1, wherein the processor calculates the characteristic amounts based on information on conditions used in an experiment performed on the cells associated with the cell image.

8. The image processing apparatus according to claim 1, wherein the processor uses sparse estimation to extract specific correlations from among the plurality of correlations among the calculated characteristic amounts, based on the likelihood of the characteristic amounts.

9. The image processing apparatus according to claim 1, wherein the processor uses sparse estimation to extract one or more specific elements from elements configuring the correlations among the calculated characteristic amounts.

10. The image processing apparatus according to claim 1, wherein the processor uses sparse estimation to compare the plurality of correlations among the calculated characteristic amounts, based on the likelihood of the characteristic amounts, to extract one or more groups of specific elements from groups of elements configuring the correlations.

* * * * *

UNITED STATES PATENT AND TRADEMARK OFFICE
CERTIFICATE OF CORRECTION

PATENT NO. : 10,796,130 B2
APPLICATION NO. : 16/060247
DATED : October 6, 2020
INVENTOR(S) : Nobuhiko Maiya et al.

It is certified that error appears in the above-identified patent and that said Letters Patent is hereby corrected as shown below:

On the Title Page

Item (72), should read:
(72) Inventors: Nobuhiko MAIYA, Yokohama-shi, (JP); Masafumi YAMASHITA, Fujisawa-shi, (JP); Shoko YAMASAKI, Tokyo, (JP); Yosuke OTSUBO, Tokyo, (JP); Shunsuke TAKEI, Yokohama-shi, (JP); Masayuki MURATA, Tokyo, (JP); Fumi KANO, Tokyo, (JP); Yoshiyuki NOGUCHI, Tokyo, (JP)

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*